(12) United States Patent
Ruoslahti et al.

(10) Patent No.: US 6,296,832 B1
(45) Date of Patent: *Oct. 2, 2001

(54) MOLECULES THAT HOME TO A SELECTED ORGAN IN VIVO

(75) Inventors: Erkki Ruoslahti, Rancho Santa Fe; Renata Pasqualini, Solana Beach, both of CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/226,985

(22) Filed: Jan. 8, 1999

Related U.S. Application Data

(63) Continuation of application No. 08/862,855, filed on Jun. 23, 1997, now Pat. No. 6,068,829, which is a continuation-in-part of application No. 08/813,273, filed on Mar. 10, 1997, now abandoned, which is a continuation-in-part of application No. 08/526,710, filed on Sep. 11, 1995, now Pat. No. 5,622,699.

(51) Int. Cl.$^7$ .............................. A61K 49/00; C12Q 1/68; C12Q 1/70

(52) U.S. Cl. ................................. 424/9.1; 424/9.2; 435/6

(58) Field of Search ........................... 424/9.1, 9.2, 9.34, 424/9.341; 435/7.1, 6

(56) References Cited

U.S. PATENT DOCUMENTS

| | | | |
|---|---|---|---|
| 4,399,124 | 8/1983 | Fauve | 514/14 |
| 4,877,599 | 10/1989 | Lees | 424/1.53 |
| 4,897,464 | 1/1990 | Vallee et al. | 530/350 |
| 5,081,034 | 1/1992 | Bevilasqua et al. | 435/252.33 |
| 5,098,833 | 3/1992 | Lasky et al. | 435/69.1 |
| 5,216,131 | 6/1993 | Lasky et al. | 530/350 |
| 5,225,538 | 7/1993 | Capon et al. | 530/387.3 |
| 5,270,163 | 12/1993 | Gold et al. | 435/6 |
| 5,288,846 | 2/1994 | Quertermous et al. | 435/455 |
| 5,304,640 | 4/1994 | Lasky et al. | 536/23.5 |
| 5,415,874 | 5/1995 | Bender et al. | 424/520 |
| 5,428,130 | 6/1995 | Capon et al. | 530/350 |
| 5,453,362 | 9/1995 | Lamarco et al. | 435/69.1 |
| 5,506,126 | 4/1996 | Seed et al. | 435/6 |
| 5,622,699 * | 4/1997 | Ruoslahti et al. | 424/93.6 |
| 5,660,827 | 8/1997 | Thorpe et al. | 424/152.1 |
| 5,688,935 | 11/1997 | Stephans et al. | 536/23.1 |
| 6,068,829 * | 5/2000 | Rouslahti et al. | 424/9.1 |

FOREIGN PATENT DOCUMENTS

| | | |
|---|---|---|
| 0135 277A | 7/1984 | (EP) . |
| 0 639 584 | 2/1995 | (EP) . |
| WO 92/00091 | 1/1992 | (WO) . |
| WO 92/03461 | 3/1992 | (WO) . |
| WO 92/06191 | 4/1992 | (WO) . |
| WO 95/14714 | 6/1995 | (WO) . |
| WO 96/34874 | 11/1996 | (WO) . |
| WO 96/34875 | 11/1996 | (WO) . |

OTHER PUBLICATIONS

Baille et al., "Tumour Vasculature—A Potential Therapeutic Target" *British J. Cancer* 72:257–267 (1995).

Burioni et al., "Recombinant Human Fab to Glycoprotein D Neutralizes Infectivity and Prevents Cell–to–Cell Transmission of Herpes Simplex Viruses 1 and 2 In Vitro," *Proc. Natl. Acad. Sci. USA* 91:355–359 (1994).

Burrows and Thorpe, "Vascular Targeting—A New Approach to the Therapy of Solid Tumors," *Pharmac. Ther.* 64:155–174 (1994).

Burton et al., "A Large Array of Human Monoclonal Antibodies to Type 1 Human Immunodeficiency Virus From Combinatorial Libraries of Asymptomatic Seropositive Individuals," *Proc. Natl. Acad. Sci. USA* 88:10134–10137 (1991).

Cattani et al., "Cloning and Characterization of Human Recombinant Antibody Fab Gragments Specific for Types 1 and 2 Herpes Simplex Virus," *Microbiologica* 18:135–142 (1995).

Cattani et al., "Cloning and Characterization of Human Recombinant Antibody Fab Gragments Specific for Types 1 and 2 *Herpes Simplex* Virus," *Chem. Abstact* 123:1015 (1995).

Davis et al., "Use of a High Affinity DNA Ligand in Flow Cytometry," *Nucl. Acids Res.* 24:702–706 (1996).

Drolet et al., "An Enzyme–linked Oligonucleotide Assay," *Nat. Biotech.* 14:1021–1025 (1996).

Dvoral et al., "Structure of Solid Tumors and Their Vasculature: Implications for Therapy with Monoclonal Antibodies," *Cancer Cells* 3:77–85 (1991).

Goetz et al., "Lu–ECAM–1–Mediated Adhesion of Melanoma Cells to Endothelium Under Conditions of Flow," *Int. J. Cancer* 65:192–199 (1996).

Gold et al., "Diversity of Oligonucleotide Functions," *Annu. Rev. Biochem.* 64:763–797 (1995).

Goodson et al., "High–Affinity Urokinase Receptor Antagonists Identified with Bacteriophage Peptide Display," *Proc. Natl. Acad. Sci. USA* 91:7129–7133 (1994).

Green et al., "Comprehensive Chemical Modification Interference and Nucleotide Substitution Analysis of an RNA Pseudoknot Inhibitor to HIV–1 Reverse Transcriptase," *J. Mol. Biol.* 247:60–68 (1995).

Hendrikx et al., "Homing of Fluuroescently Labeled Murine Hematopoietic Stem Cells," *Expt. Hematol.* 24:129–140 (1996).

Hicke et al., "DNA Aptamers Block L–Selection Function In Vivo," *J. Clin. Invest.* 98:2688–2692 (1996).

Huang et al., "Tumor Infarction in Mice by Antibody–Directed Targeting of Tissue Factor to Tumor Vasulature," *Science* 275:547–550 (1997).

(List continued on next page.)

Primary Examiner—Scott D. Priebe
(74) Attorney, Agent, or Firm—Campbell & Flores LLP

(57) ABSTRACT

The present invention provides enriched library fractions containing a plurality of molecules that home to a selected organ in vivo.

10 Claims, No Drawings

OTHER PUBLICATIONS

Lappi, Douglas A., "Tumor Targeting Through Fibroblast Growth Factor Receptors," *Cancer Biology* 6:279–288 (1995).

Leff, D., "NeXster Previews 'PASS' for Downstream Synthesis of Therapeutic Oligos," *Bioworld Today* 8:2&4 (1997).

Martiny–Baron and Marmé, "VEGF–mediated Tumour Angiogenesis: A New Target for Cancer Therapy," *Current Biology* 6:675–680 (1995).

Miner et al., "Clonal Drift of Cell Surface, Melanogenic, and Experimental Metastatic Properties of in vivo–selected, Brain Meninges–colonizing Murine B16 Melanoma," *Cancer research* 42:4631–4638 (1982).

Nakano et al., "Genetic Defeact in T Lymphocyte–Specific Homing into Peripheral Lymph Nodes," *Eur. J. Immunol.* 27:215–221 (1997).

Pasqualini and Ruoslahti, "Searching for a Molecular Address in the Brain; Tissues Targeting with Phage Peptide Libraries," *Mol. Psych.* 1:421–423 (1996).

Pasqualini et al., "αv Integrins as Receptors for Tumor Targeting by Circulating Ligands, " *Nature Biotechnol.* 15:542–548 (1997).

Pasqualini and Ruoslahti, "Organ Targeting in vivo using Phage Display Peptide Libraries," *Nature* 380:364–366 (1996).

Pauli et al., "Organ–preference of Metastasis," *Cancer and Metastasis reviews* 9:175–189 91990).

Smith et al., "Studies on the Use of Viruses in the Treatment of Carcinoma of the Cervix," *Cancer* 9:1211–1218 (1956).

Zhu et al., "Mediation of Lung Metastasis of Murine Melanomas by a Lung–specific Endothelial cell Adhesion Molecule," *Proc. Natl. Acad.* 88:9568–9572 (1991).

The 1996 NEXSTAR Annual Report.

* cited by examiner

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:1:

Cys Asn Ser Arg Leu His Leu Arg Cys
1               5

(2) INFORMATION FOR SEQ ID NO:2:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:2:

Cys Glu Asn Trp Trp Gly Asp Val Cys
1               5

(2) INFORMATION FOR SEQ ID NO:3:

(i) SEQUENCE CHARACTERISTICS:
      (A) LENGTH: 9 amino acids
      (B) TYPE: amino acid
      (D) TOPOLOGY: circular (ii) MOLECULE TYPE: peptide (xi) SEQUENCE DESCRIPTION: SEQ ID NO:3:

Cys Leu Ser Ser Arg Leu Asp Ala Cys
1               5

(2) INFORMATION FOR SEQ ID NO:4:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:4:

Cys Val Leu Arg Gly Gly Arg Cys
1               5

(2) INFORMATION FOR SEQ ID NO:5:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:5:

Cys Asn Ser Arg Leu Gln Leu Arg Cys
1               5

(2) INFORMATION FOR SEQ ID NO:6:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:6:

Cys Gly Val Arg Leu Gly Cys
1               5

(2) INFORMATION FOR SEQ ID NO:7:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:7:

Cys Lys Asp Trp Gly Arg Ile Cys
1               5

(2) INFORMATION FOR SEQ ID NO:8:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:8:

```
Cys Leu Asp Trp Gly Arg Ile Cys
1               5
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:9:

```
Cys Thr Arg Ile Thr Glu Ser Cys
1               5
```

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:10:

```
Cys Glu Thr Leu Pro Ala Cys
1               5
```

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:11:

```
Cys Arg Thr Gly Thr Leu Phe Cys
1               5
```

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:12:

```
Cys Gly Arg Ser Leu Asp Ala Cys
1               5
```

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

```
Cys Arg His Trp Phe Asp Val Val Cys
1               5
```

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

```
Cys Ala Asn Ala Gln Ser His Cys
1               5
```

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:15:

```
Cys Gly Asn Pro Ser Tyr Arg Cys
1               5
```

(2) INFORMATION FOR SEQ ID NO:16:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:16:

```
Trp Arg Cys Val Leu Arg Glu Gly Pro Ala Gly Gly Cys Ala Trp Phe
1               5                   10                  15

Asn Arg His Arg Leu
            20
```

(2) INFORMATION FOR SEQ ID NO:17:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:17:

```
Tyr Pro Cys Gly Gly Glu Ala Val Ala Gly Val Ser Ser Val Arg Thr
1               5                   10                  15

Met Cys Ser Glu
            20
```

(2) INFORMATION FOR SEQ ID NO:18:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:18:

```
Leu Asn Cys Asp Tyr Gln Gly Thr Asn Pro Ala Thr Ser Val Ser Val
```

```
1               5                  10                 15
Pro Cys Thr Val
                20
```

(2) INFORMATION FOR SEQ ID NO:19:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:19:

```
Leu Ser Ser Arg Leu Asp Ala
1               5
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

```
Val Leu Arg Glu Gly Pro Ala Gly Gly
1               5
```

(2) INFORMATION FOR SEQ ID NO:21:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:21:

```
Cys Leu Pro Val Ala Ser Cys
1               5
```

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:22:

```
Cys Gly Ala Arg Glu Met Cys
1               5
```

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:23:

```
Cys Lys Gly Arg Ser Ser Ala Cys
1               5
```

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:24:

Cys Trp Ala Arg Ala Gln Gly Cys
1               5

(2) INFORMATION FOR SEQ ID NO:25:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:25:

Cys Leu Gly Arg Ser Ser Val Cys
1               5

(2) INFORMATION FOR SEQ ID NO:26:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:26:

Cys Thr Ser Pro Gly Gly Ser Cys
1               5

(2) INFORMATION FOR SEQ ID NO:27:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:27:

Cys Met Gly Arg Trp Arg Leu Cys
1               5

(2) INFORMATION FOR SEQ ID NO:28:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:28:

Cys Val Gly Glu Cys Gly Gly Cys
1               5

(2) INFORMATION FOR SEQ ID NO:29:

```
    (i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:29:

Cys Val Ala Trp Leu Asn Cys
1               5

(2) INFORMATION FOR SEQ ID NO:30:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:30:

Cys Arg Arg Phe Gln Asp Cys
1               5

(2) INFORMATION FOR SEQ ID NO:31:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:31:

Cys Leu Met Gly Val His Cys
1               5

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:32:

Cys Lys Leu Leu Ser Gly Val Cys
1               5

(2) INFORMATION FOR SEQ ID NO:33:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:33:

Cys Phe Val Gly His Asp Leu Cys
1               5

(2) INFORMATION FOR SEQ ID NO:34:

(i) SEQUENCE CHARACTERISTICS:
        (A) LENGTH: 7 amino acids
        (B) TYPE: amino acid
        (D) TOPOLOGY: linear
```

(ii) MOLECULE TYPE: peptide (xi) SEQUENCE DESCRIPTION: SEQ ID NO:34:

Cys Arg Cys Leu Asn Val Cys
1               5

(2) INFORMATION FOR SEQ ID NO:35:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:35:

Cys Lys Leu Met Gly Glu Cys
1               5

(2) INFORMATION FOR SEQ ID NO:36:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:36:

Cys Xaa Xaa Xaa Xaa Xaa Cys
1               5

(2) INFORMATION FOR SEQ ID NO:37:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:37:

Cys Xaa Xaa Xaa Xaa Xaa Xaa Cys
1               5

(2) INFORMATION FOR SEQ ID NO:38:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:38:

Cys Xaa Xaa Xaa Xaa Xaa Xaa Xaa Cys
1               5

(2) INFORMATION FOR SEQ ID NO:39:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:39:

```
Cys Xaa Xaa Xaa Xaa Xaa Xaa Xaa Xaa Xaa
1               5                   10
```

(2) INFORMATION FOR SEQ ID NO:40:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:40:

```
Xaa Xaa Cys Xaa Xaa Xaa Xaa Xaa Xaa Xaa Xaa Xaa Xaa Xaa Xaa
1               5                   10                  15

Xaa Cys Xaa Xaa
        20
```

(2) INFORMATION FOR SEQ ID NO:41:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:41:

```
Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa
        20
```

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
TGTNNKNNKN NKNNKNNKTG T                                     21
```

(2) INFORMATION FOR SEQ ID NO:43:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:43:

```
Cys Val Arg Leu Asn Ser Leu Ala Cys
1               5
```

(2) INFORMATION FOR SEQ ID NO:44:

(i) SEQUENCE CHARACTERISTICS:
        (A) LENGTH: 4 amino acids
        (B) TYPE: amino acid
        (D) TOPOLOGY: linear (ii) MOLECULE TYPE: peptide

```
(xi) SEQUENCE DESCRIPTION: SEQ ID NO:44:

Asp Xaa Xaa Arg
```

MOLECULES THAT HOME TO A SELECTED ORGAN IN VIVO

This application is a continuation of application U.S. Ser. No. 08/862,855, filed Jun. 23, 1997, now U.S. Pat. No. 6,068,829, which is a continuation-in-part of U.S. Ser. No. 08/813,273 filed Mar. 10, 1997, now abandoned which is a continuation-in-part of U.S. Ser. No. 08/526,710, filed Sep. 11, 1995, now U.S. Pat. No. 5,622,699.

This invention was made with government support under CA 42507, CA 62042 and Cancer Center Support Grant CA 30199 awarded by the National Institutes of Health. The government has certain rights in this invention.

BACKGROUND OF THE INVENTION

1. Field of the Invention

The present invention relates generally to the fields of molecular medicine and drug delivery and, more specifically, to a method of in vivo panning for identifying a molecule that homes to a specific organ.

2. Background Information

Although the effect of a particular pathology often is manifest throughout the body of the afflicted person, generally, the underlying pathology may affect only a single organ or tissue. In many cases, drugs are the treatment of choice for a patient suffering a particular disease. It is rare, however, that a drug will target only the diseased tissue or organ. More commonly, drug treatment results in undesirable side effects due, for example, to generalized toxic effects throughout the patient's body. The nausea, loss of hair and drop in blood count that occur as a result of treating of a cancer patient with chemotherapeutic agents are examples of the undesirable side effects that can occur due to drug treatment The undesirable side effects that can occur when drugs are used to treat a disease most often are due to the inability of the drug to specifically target the diseased organ or tissue. For example, a cancer chemotherapeutic agent that targets rapidly proliferating cells would be useful to kill rapidly dividing cancer cells. However, such an agent also kills normal proliferating hematopoietic and epithelial cells. Thus, the dose of such a drug that can be administered to a patient is limited due to its toxic effect on normal cells.

Efforts have been made to increase the target specificity of various drugs. In some cases, a particular cell type present in a diseased tissue or organ may express a unique cell surface marker. In such a case, an antibody can be raised against the unique cell surface marker and a drug can be linked to antibody Upon administration of the drug/antibody complex to the patient, the binding of the antibody to the cell surface marker results in the delivery of a relatively high concentration of the drug to the diseased tissue or organ. Similar methods can be used where a particular cell type in the diseased organ expresses a unique cell surface receptor or a ligand for a particular receptor. In these cases, the drug can be linked to the specific ligand or to the receptor, respectively, thus providing a means to deliver a relatively high concentration of the drug to the diseased organ.

While linking a drug to a molecule that homes to a particular cell type present in a diseased organ or tissue provides significant advantages for treatment over the use of a drug, alone, use of this method is severely limited. In particular, very few cell type specific antibodies have been described and it can be difficult and time consuming to attempt to obtain an antibody that targets an organ in a particular patient suffering a pathology. Furthermore, few cell type specific surface markers have been described. Even where such markers have been described, the cells expressing the markers can be distributed among various tissues or organs, thereby limiting their usefulness as targets. Thus, it is important to identify specific target cell markers that are expressed in only one or a few tissues or organs and to identify molecules that specifically interact with such markers.

Various cell types can express unique markers and, therefore, provide potential targets for organ homing molecules. Endothelial cells, for example, which line the internal surfaces of blood vessels, can have distinct morphologies and biochemical markers in different tissues. The blood vessels of the lymphatic system, for example, express various adhesion proteins that serve to guide lymphocyte homing. For example, endothelial cells present in lymph nodes express a cell surface marker that is a ligand for L-selectin and endothelial cells in Peyer's patch venules express a ligand for the $\alpha_4\beta_7$ integrin. These ligands are involved in specific lymphocyte homing to their respective lymphoid organs. Thus, linking a drug to L-selectin or to the $\alpha_4\beta_7$ integrin may provide a means for targeting the drug to diseased lymph nodes or Peyer's patches, respectively, provided that these molecules do not bind to similar ligands present in a significant number of other organs.

Although the homing molecules present in the blood vessels of non-lymphoid tissues have not been clearly defined, the ability of lymphocytes to return to the organ in which they were first stimulated indicates that organ-specific endothelial markers exist. Similarly, the homing or metastasis of particular types of tumor cells to specific organs provides further evidence that organ-specific markers exist. However, there remains a need to identify other organ-specific cell markers and the molecules that bind to them.

Methods are now available for producing large populations of molecules. In addition, methods are available for screening libraries of molecules to identify those of interest. For example, phage peptide display libraries can be used to express large numbers of peptides that can be screened in vitro with a particular target molecule or a cell of interest in order to identify peptides that specifically bind the target molecule or the cell. Screening of such phage display libraries has been used, for example, to identify ligands that specifically bind various antibodies and cell surface receptors.

Screening of a phage display library generally involves in vitro panning of the library using a purified target molecule. Phage that bind the target molecule can be recovered, individual phage can be cloned and the peptide expressed by a cloned phage can be determined. Such a peptide can be useful for delivery of a drug linked to the peptide to cells expressing the target molecule.

Unfortunately, very few target molecules that are expressed by only one or a few cell types have been identified. Furthermore, even where such a target molecule is known, it is uncertain whether a peptide that specifically binds the target molecule, as determined using an in vitro panning method, will bind to the target molecule in vivo. As a result, the identification of a peptide from a phage display library using an in vitro panning method essentially represents only a starting point for determining whether the identified peptide can be useful for an in vivo procedure. Thus, a need exists to develop in vivo methods for screening large numbers of molecules such as peptides in order to identify those that can home to one or more selected organs. The present invention satisfies this need and provides related advantages as well.

SUMMARY OF THE INVENTION

The present invention provides a method of identifying a molecule that homes specifically to one or a few selected organs by using in vivo panning to screen a library of potential organ homing molecules. The in vivo panning method involves administering a library, which consists of a diverse population of molecules, to a subject and identifying molecules that home to one or more selected organs in the subject. The invention is exemplified by administration of a phage peptide display library to a subject and the identification of peptides expressed by phage that home to brain or to kidney in the subject. In vivo panning can be repeated one or more times until a molecule that homes to a selected organ with the desired selectivity is recovered.

The invention also provides methods of identifying a target molecule by detecting selective binding of the target molecule to a peptide of the invention. For example, a peptide that selectively homes to a selected organ can be attached to a solid matrix for use in affinity chromatography. A sample of the organ can be obtained and passed over the affinity matrix under conditions that allow specific binding of the target molecule, which then can be collected and identified using well known biochemical methods. The target molecule can be useful, for example, for raising an antibody specific for the target molecule.

DETAILED DESCRIPTION OF THE INVENTION

The present invention provides a method of identifying a molecule that homes specifically to one or a few selected organs by screening a library using in vivo panning. The identified molecules are useful, for example, for targeting a desired moiety such as a drug, a toxin or a detectable label, which can be linked to the molecule, to the selected organ. In vivo panning provides a direct means for identifying molecules that specifically home to a selected organ and, therefore, provides a significant advantage over previous methods, which require that a molecule identified using an in vitro screening method subsequently be examined to determine whether it maintains its specificity in vivo.

As used herein, the term "library" means a collection of molecules. A library can contain a few or a large number of different molecules, varying from about ten molecules to several billion molecules or more. If desired, a molecule can be linked to a tag, which can facilitate recovery or identification of the molecule.

As used herein, the term "molecule" is used broadly to mean an organic chemical such as a drug; a peptide, including a variant or modified peptide or peptide-like molecules such as a peptidomimetic or peptoid; or a protein such as an antibody or a growth factor receptor or a fragment thereof such as an Fv, Fd or Fab fragment of an antibody, which contains a binding domain. For convenience, the term "peptide" is used broadly herein to mean peptides, proteins, fragments of proteins, and the like. A molecule can be a non-naturally occurring molecule, which does not occur in nature, but is produced as a result of in vitro methods, or can be a naturally occurring molecule such as a protein or fragment thereof expressed from a cDNA library.

Methods for preparing libraries containing diverse populations of various types of molecules such as peptides, peptoids or peptidomimetics are well known in the art and commercially available (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which is produced in vitro. Methods of synthetic peptide and nucleic acid chemistry are well known in the art.

A library of molecules also can be produced, for example, by constructing a cDNA expression library from mRNA collected from a cell, tissue, organ or organism of interest. Methods for producing such libraries are well known in the art (see, for example, Sambrook et al., *Molecular Cloning: A laboratory manual* (Cold Spring Harbor Laboratory Press 1989), which is incorporated herein by reference). Preferably, the peptide encoded by the cDNA is expressed on the surface of a cell or a virus containing the cDNA. For example, cDNA can be cloned into a phage vector such as fuse 5 (see Example I), wherein, upon expression, the encoded peptide is expressed as a fusion protein on the surface of the phage.

As disclosed herein, in vivo panning comprises administering a library to a subject, collecting a selected organ and identifying an organ homing molecule. An organ homing molecule can be identified using various methods well known in the art. Generally, the presence of an organ homing molecule in a collected organ is identified based on one or more characteristics common to the molecules present in the library, then the structure of a particular organ homing molecule is identified. For example, a highly sensitive detection method such as mass spectrometry, either alone or in combination with a method such as gas chromatography, can be used to identify organ homing molecules in a selected organ. Thus, where a library comprises diverse molecules based generally on the structure of an organic molecule such as a drug, an organ homing molecule can be identified by determining the presence of a parent peak for the particular molecule.

If desired, the selected organ can be processed using a method such as HPLC, which can provide a fraction enriched in molecules having a defined range of molecular weights or polar or nonpolar characteristics or the like. Conditions for HPLC will depend on the chemistry of the particular molecule and are well known to those skilled in the art. Similarly, methods for bulk removal of potentially interfering cellular materials such as DNA, RNA, proteins, lipids or carbohydrates are well known in the art as are methods for enriching a fraction containing an organic molecule using, for example, methods of selective extraction. For example, where a library comprises a population of diverse organic chemical molecules each linked to a unique oligonucleotide tag, such that the specific molecule is identified by determining the oligonucleotide sequence using PCR, genomic DNA can be removed from the sample of the collected organ in order to reduce the potential for background PCR reactions. These and other methods can be useful for enriching the sample of the collected organ for the particular organ homing molecule, thereby removing potentially contaminating materials from the collected organ sample and increasing the sensitivity of detecting a molecule.

Evidence provided herein indicates that a sufficient number of organ homing molecules selectively home to a selected organ during in vivo panning such that the molecules readily can be identified. For example, various independent phage expressing the same peptide were identified in brain and in kidney (see Tables 1 and 2). Specifically, almost half of the kidney homing peptides that were sequenced had the amino acid sequence CLPVASC (SEQ ID NO: 21). Similarly, two peptides that homed to brain constituted about 40% of the sequenced brain homing peptides. Thus, a substantial fraction of the identified organ homing molecules can have the same structure. Furthermore. the peptide inserts of only a small number of isolated phage were determined. However, following various in vivo pannings for brain and kidney homing molecules, hundreds of thousands to millions of phage expressing organ homing peptides were recovered from the respective organs. These results indicate that some organ homing molecules will be present in substantial numbers in an organ following in vivo homing, thereby increasing the ease with which the molecules can be identified.

Ease of identification of an organ homing molecule depends on various factors, including the presence of potentially contaminating background cellular material. For example, where the organ homing molecule is an untagged peptide, a larger number must home to the organ in order to identify the specific peptides against the background of cellular protein. In contrast, a much smaller number of an untagged organic chemical homing molecule such as a drug is identifiable because such molecules normally are absent from or present in only small numbers in the body. In such a case, a highly sensitive method such as mass spectrometry can be used to identify an organ homing molecule. The skilled artisan will recognize that the method of identifying a molecule will depend, in part, on the chemistry of the particular molecule.

The molecules of a library also can be present as a conjugate, which can facilitate recovery or identification of the molecule. As used herein, the term "conjugate" or "molecule conjugate" means a molecule of the library linked to a physical, chemical or biological tag such as a plastic microbead, an oligonucleotide or a bacteriophage, respectively. The tag can provide a means to identify or recover an organ homing molecule of the invention following in vivo panning. For example, a conjugate can be a molecule such as a peptide linked to a unique oligonucleotide tag (see, for example, Brenner and Lerner, *Proc. Natl. Acad. Sci., USA* 89:5381–5383 (1992), which is incorporated herein by reference). Upon homing to an organ, the particular peptide can be identified by performing PCR on a sample of the organ containing the conjugate under conditions that allow amplification of the oligonucleotide tag (see, for example, Erlich, *PCR Technology: Principles and Applications for DNA Amplification* (Stockton Press 1989), which is incorporated herein by reference). By determining the oligonucleotide sequence, the identity of the peptide can be determined.

In addition, a tag can be a support. As used herein, the term "support" means a tag having a defined surface to which a molecule can be attached. For example, a support can be a biological tag such as a virus or virus-like particle such as a bacteriophage ("phage"); a bacterium such as *E. coli*; or a eukaryotic cell such as a yeast, insect or mammalian cell; or can be a physical tag such as a liposome or a microbead, which can be composed of a plastic, agarose, gelatin or other material. In general, a support should have a diameter less than about 10 $\mu$m to about 50 $\mu$m in its shortest dimension, such that the support can pass relatively unhindered through the capillary beds present in the subject and not occlude circulation. In addition, a support can be nontoxic and biodegradable, particularly where the subject used for in vivo panning is not sacrificed to collect a selected organ.

Where a molecule is linked to a support, the conjugate comprises the molecule attached to the surface of the support, such that the part of the molecule suspected of being able to interact with a target in a cell in the subject is positioned so as be able to participate in the interaction. For example, where the molecule is suspected of being a β adrenergic agonist, the binding portion of the molecule attached to a support is positioned so it can interact with a β adrenergic receptor on a cell in the selected organ. Similarly, where the molecule is suspected of being a ligand for a growth factor receptor, the molecule is positioned on the support so that it can bind the receptor.

As exemplified herein, a peptide suspected of being able to home to a selected organ such as brain was expressed as the N-terminus of a fusion protein, wherein the C-terminus consisted of a phage coat protein. Upon expression of the fusion protein, the C-terminal coat protein linked the fusion protein to the surface of a phage such that the N-terminal peptide was in a position to interact with a target molecule in an organ. Thus, a conjugate was formed by the linking of a peptide molecule to a phage, wherein the phage provided a biological support and the peptide molecule is linked as a fusion protein.

As used herein, the term "in vivo panning" means a method of screening a library by administering the library to a subject and identifying a molecule that selectively homes to one or a few selected organs. The term "administering to a subject", when used in referring to a library of molecules or a portion thereof, is used in its broadest sense to mean that the library is delivered to a selected organ. For example, a library can be administered to a subject by injecting the library into the circulation of the subject such that the molecules can pass through the selected organ; after an appropriate period of time, circulation is terminated by sacrificing the subject or by removing a sample of the organ (see Example I). Alternatively, a cannula can be inserted into a blood vessel in the subject, such that the library is administered by perfusion for an appropriate period of time, after which the library can be removed from the circulation through the cannula or the subject can be sacrificed or the organ can be sampled to terminate circulation. Similarly, a library can be shunted through one or a few organs by cannulation of the appropriate blood vessels in the subject. It is recognized that a library also can be administered to an isolated perfused organ. Such panning in an isolated perfused organ can be useful for identifying molecules that bind to the organ and, if desired, can be used as an initial screening of a library. For example, if a kidney homing molecule is desired, a library can be perfused through an isolated kidney, then the molecules that bound to the perfused kidney can be screened by in vivo panning to identify a kidney homing molecule.

The in vivo panning method is exemplified herein by screening a phage peptide display library in mice and identifying specific peptides that selectively home to brain or to kidney (see Examples I and II). However, phage libraries that display protein receptor molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site-directed or codon based mutagenesis (see Huse, U.S. Pat. No. 5,264,563, issued Nov. 23, 1993, which is incorporated herein by reference). Thus, various types of phage display libraries can be screened using the disclosed in vivo panning method.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (*Meth. Enzymol.* 217:228–257 (1993); see, also, Scott and Smith, *Science* 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference; see, also, Example I). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the in vivo panning method of the invention in order to identify a peptide that homes to one or a few selected organs.

In addition, to screening a phage display library, in vivo panning can be used to screen various other types of libraries, including, for example, an RNA or cDNA library or a chemical library. If desired, the organ homing molecule can be in the form of a conjugate, which can facilitate recovery of the molecule from a selected organ or identification of the molecule in the organ. For example, where the molecules of a tagged chemical library are screened, the tag can be a moiety such as biotin, which can be linked directly to the molecule or can be linked to a support containing the molecules. Biotin provides a means to recover the molecule from a selected organ using an avidin or streptavidin affinity matrix. In addition, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the molecule. Methods for purifying biotin or phox labeled conjugates are known in the art and the materials for performing these procedures are commercially available (eg., Invitrogen; La Jolla Calif.; and Promega Corp.; Madison Wis.). In the case where a phage library is screened, the phage can be recovered using methods as disclosed in Example I.

In vivo panning provides a method for directly identifying molecules that can home to one or a few selected organs. As used herein, the term "home" or "selectively home" means that a particular molecule binds relatively specifically to a target molecule present in one or few selected organs following administration to a subject. In general, selective homing is characterized, in part, by detecting at least a 2-fold (2×) greater specific binding of the molecule to the selected organ as compared to a control organ. It should be recognized that, in some cases, a molecule can localize non-specifically to an organ, Non-specific localization can be distinguished from homing by performing competition experiments such as those described in Examples II.C. and II.D.

Selective homing can be demonstrated by determining the specificity of an organ homing molecule for the selected organ as compared to a control organ. For example, a ratio of brain:kidney homing of up to 9:1 was observed for brain homing peptides (i.e., 9× greater binding to the selected organ as compared to the control organ; see Example II).

Selective homing also can be demonstrated by showing that molecules that home to a selected organ, as identified by one round of in vivo panning, are enriched for organ homing molecules in a subsequent round of in vivo panning. For example, phage expressing peptides that selectively home to brain were isolated by in vivo panning, then were subjected to additional rounds of in vivo panning. As demonstrated in Example II, phage recovered from brain after a first round of screening showed an 8× enrichment in homing to brain as compared to kidney following a second round of screening and a 13× enrichment following a third round of in vivo panning. When a peptide that selectively homes to brain was linked to a moiety, i.e., a red blood cell (RBC), the peptide/RBC complex selectively homed to brain (see Example II.D.).

Due to the conserved nature of cellular receptors and of ligands that bind a particular receptor, the skilled artisan would recognize that an organ homing molecule identified using, for example, in vivo panning in a mouse also would bind to the corresponding target molecule in the selected organ of a human or other species. For example, an RGD-containing peptide that can specifically bind to an integrin expressed by a cell in a human subject also can bind integrins expressed in a variety of species, including integrins expressed in mammalian cells such as murine and bovine cells as well as in cells of more evolutionarily distant species such as Drosophila. The ability of an organ homing molecule identified using in vivo panning in an experimental animal such as a mouse readily can be examined for the ability to bind to the corresponding organ in a human subject by demonstrating, for example, that the molecule also can bind specifically in vitro to a sample of the selected organ obtained from a human subject. Thus, routine methods can be used to confirm that an organ homing molecule identified using in vivo panning in an experimental animal also can bind an organ-specific target molecule in a human subject.

The steps of administering the library to the subject, collecting a selected organ and identifying the molecules that home to the selected organ, comprise a single round of in vivo panning. Although not required, one or more additional rounds of in vivo panning generally are performed. Where an additional round of in vivo panning is performed, the molecules recovered from the selected organ in the previous round are administered to a subject, which can be the same subject used in the previous round, where only a part of the selected organ was collected.

By performing a second round of in vivo panning, the relative binding selectivity of the molecule conjugates recovered from the first round can be determined by administering the identified molecule conjugates to a subject, collecting the selected organ and a control organ, and comparing the molecules recovered from the selected organ with those recovered from a control organ. In addition, a second round of in vivo panning can indicate whether the molecules identified from the initially selected organ also can home to additional organs, thus defining a family of selected organs. Additional rounds of panning can be performed as desired.

Ideally, no molecules are recovered from a control organ following a second or subsequent round of in vivo panning. Generally, however, a proportion of the molecules also will be present in a control organ. In this case, the ratio of molecules in the selected organ as compared to the control organ (selected:control) can be determined. As described above, for example, phage that homed to brain following a first round of in vivo panning demonstrated a 13× enrichment in homing to the selected organ as compared to the control organ, kidney, following two additional rounds of panning (Example II).

Additional rounds of in vivo panning can be used to determine whether a particular molecule homes only to the selected organ or can recognize a target on the selected organ that also is expressed in one or more other organs or is sufficiently similar to the target in the originally selected organ. Where a molecule is found to direct homing to organs in addition to the originally selected organ, the organs are considered to constitute a family of selected organs. Using the method of in vivo panning, molecules that home to only a single selected organ and molecules that home to a family of selected organs can be defined. Such identification is expedited by collecting various organs during subsequent rounds of in vivo panning.

As used herein, the term "selected organ" is used in its broadest sense to mean an organ to which a molecule selectively homes. In addition, the term "organ" is used broadly to mean organ, tissue or cell type, including a cancer cell, in which case the selected organ can be a tumor such as a primary tumor or a metastatic lesion. In general, a selected organ contains a cell that expresses a particular target molecule such as a cell surface receptor to which an organ homing molecule can bind. By performing at least two rounds of in vivo panning, the selectivity of homing of the molecule to the selected organ can be determined (see Example II). As discussed above, however, in some cases an organ homing molecule can selectively home to more than one selected organ, in which case the molecule is considered to be able to selectively home to a family of selected organs.

The term "control organ" is used to mean an organ other than a selected organ. A control organ is characterized by the inability of an organ homing molecule to home to the control organ. A control organ is useful for identifying non-specific binding of a molecule. A control organ can be collected, for example, to identify non-specific binding of the molecule or to determine the selectivity of homing of the molecule (see Examples I and II). In addition, non-specific binding can be identified by administering, for example, a control molecule, which is known not to home to an organ but is chemically similar to a potential organ homing molecule. Alternatively, where the molecules are administered as a conjugate comprising the molecules of the library linked to a support, administration of the supports, alone, can be used to identify non-specific binding. For example, a phage that expresses the gene III protein, alone, but that does not contain a peptide fusion protein, can be screened by in vivo panning to determine the level of non-specific binding of the phage support.

In some cases it can take several rounds of in vivo panning to identify a control organ, since a molecule that selectively homes to an originally selected organ also may have the ability to selectively home to additional organs, thus defining a family of selected organs. The ability of a molecule to home to one or to a family of selected organs allows for the preparation of panels of organ homing molecules, wherein individual molecules variously home to one selected organ or to any of a family of selected organs with variable selectivity.

In general, a library of molecules, which contains a diverse population of random or selectively randomized molecules of interest, is prepared, then administered to a subject. At a selected time after administration, the subject is sacrificed and a selected organ or part of the organ is collected such that the molecules present in the selected organ can be identified. For example, a mouse was injected with a phage peptide display library, then, after about 1 to 4 minutes, the mouse was frozen in liquid nitrogen to terminate circulation of the phage, the selected organ (brain or kidney) was collected, phage present in the selected organ were recovered and peptides that selectively homed to the selected organ were identified (see Examples I and II).

In the examples provided, the animals were sacrificed to collect the selected organ. It should be recognized, however, that only a part of the selected organ need be collected to recover a support containing a molecule that homes to that organ. For example, a part of the selected organ can be collected by biopsy, such that a molecule such as a peptide expressed by a phage, can be administered to the same subject a second time or more, as desired. Where the molecule that is to be administered a second time to the same subject is linked, for example, to a support, the support must be nontoxic and should be biodegradable, so as not to interfere with subsequent rounds of screening.

In vitro screening of phage libraries previously has been used to identify peptides that bind to antibodies or to cell surface receptors (Smith and Scott, supra, 1993). For example, in vitro screening of phage peptide display libraries has been used to identify novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994)). However, such in vitro studies provide no insight as to whether a peptide that can specifically bind to a selected receptor in vitro also will bind the receptor in vivo or whether the binding peptide or the receptor are unique to a specific organ in the body. Furthermore, the in vitro methods are performed using defined, well-characterized target molecules in an artificial system. For example, Goodson et al. utilized cells expressing a recombinant urokinase receptor. Thus, the in vitro methods require prior knowledge of the target molecule and yield little if any information regarding in vivo utility. In contrast, the in vivo panning method disclosed herein requires no prior knowledge or availability of a target molecule. Thus, in vivo panning provides a significant advantage over previous methods by identifying molecules that selectively home in vivo to a target molecule present in one or a few organs.

Brain and kidney were selected as target organs to identify phage expressing peptides that selectively home to these selected organs because the blood vessels in these organs have unique characteristics. For example, the blood vessels in the brain form the "blood-brain barrier" and express at least one specific antigen (Schlosshauer and Herzog, *J. Cell Biol.* 110:1261–1274 (1990)). Using in vivo panning, phage expressing various pepcides that selectively homed to brain or to kidney, but not to both organs, were identified (see Example II). Since the in vivo panning was terminated about one to four minutes after intravenous administration of the phage to the mice, the majority of phage likely remained in the vasculature, indicating the displayed peptides bound to endothelial cell surface markers that are expressed in an organ-specific manner (see, for example, Springer, *Cell* 76:301–314 (1994)). Organ-specific homing of tumor cells and of lymphocytes indicates that the vascular beds in various tissues express unique target molecules. For example, the ability of lymphocytes to return to the organ in which they were first stimulated (Salmi et al., *Proc. Natl. Acad. Sci., USA* 89:11436–11440 (1992)) and the ability of particular types of tumor cells to home or metastasize to specific organs (Fidler and Hart, *Science* 217:998–1003 (1982)) indicate that organ-specific targets are expressed in a subject.

The identification of brain homing and kidney homing peptides demonstrates that organ-specific target molecules exist and indicates that the disclosed method of in vivo panning can be used to identify molecules that selectively home to other organs. For example, tumor vasculature which undergoes active angiogenesis and contains specific markers (Brooks et al., *Cell* 79:1157–1164 (1994)), is a particularly attractive target. The identification of molecules that home to tumor vasculature would provide a means for directing a therapeutic agent directly to a tumor while sparing normal tissues.

Phage peptide display libraries were constructed essentially as described Smith and Scott (supra, 1993; see, also, Koivunen et al., *Biotechnology* 13:265–270 (1995), which is incorporated herein by reference). Oligonucleotides encoding peptides having substantially random amino acid sequences were synthesized based on an "NNK" codon, wherein "N" is A, T, C or G and "K" is G or T. "NNK" encodes 32 triplets, which encode the twenty amino acids and an amber STOP codon (Scott and Smith, supra, 1990). At least one codon encoding cysteine also was included in each oligonucleotide so that cyclic peptides could be formed through disulfide linkages (see Example I). The oligonucleotides were inserted in frame with the sequence encoding the gene III protein (gIII) in the vector fuse 5 such that a peptide-gIII fusion protein can be expressed. Following expression, the fusion protein is expressed on the surface of the phage containing the vector (Smith and Scott, supra, 1993; Koivunen et al., supra, 1994b).

Remarkably, following in vivo panning, the phage that selectively homed to brain or to kidney displayed only a few different peptide sequences. In some cases, peptides having the same amino acid sequence were encoded by phage having different oligonucleotide sequences encoding the peptide. Furthermore, a family of brain homing peptides was identified, wherein each peptide in the family contained the common amino acid motif, SRL (serine-arginine-leucine), but different flanking amino acid sequences (see Table 1; SEQ ID NOS: 1, 3 and 5). In addition, two different peptides displayed the motif VLR (valine-leucine-arginine; see Table 1, SEQ ID NOS: 4 and 16). These results demonstrate that it is the peptide displayed by the phage, rather than some incidental mutant property of the phage, that directs homing to the selected organ. For example, the present invention was used to identify various organ homing peptides, including brain homing peptides such as CNSRLHLRC (SEQ ID NO: 1), CENWWGDVC (SEQ ID NO: 2), WRCVLREGPAG-GCAWFNRHRL (SEQ ID NO: 16) and others as shown in Table 1, and kidney homing peptides such as CLPVASC (SEQ ID NO: 21), CGAREMC (SEQ ID NO: 22) and others as shown in Table 2.

The sequences of the brain and kidney homing motifs do not reveal any significant similarities with known ligands for endothelial cell receptors nor do they resemble any sequences listed in various data banks. However, some of the brain-homing motifs share a similarity with integrin-binding sequences. For example, one brain homing peptide contained an RLD sequence, which is recognized by certain integrins (Altieri et al., *J. Biol. Chem.* 265:12119–12122 (1990); Koivunen et al., supra, 1994a), and the DXXR (SEQ ID NO: 44) motif in another peptide resembles the RGD, DGR, and NGR motifs that bind to certain integrins (Ruoslahti, *J. Clin. Invest.* 87:1–5 (1991); Koivunen et al., supra, 1994a).

Selective homing of a molecule such as a peptide or protein to a selected organ can be due to specific recognition by the peptide of a particular cell target molecule such as a cell surface receptor present on a cell in the organ. Selectivity of homing is dependent on the particular target molecule being expressed on only one or a few different cell types, such that the molecule homes to only one or a few organs. As discussed above, brain and kidney homing peptides likely are recognizing endothelial cell surface markers in the blood vessels present in these organs. However, most different cell types, particularly cell types that are unique to an organ, can express unique target molecules. Thus, in organs such as liver, spleen or lymph node, where blood circulates through sinusoids formed by the cells specific for the organ, in vivo panning can be useful for identifying molecules that home to the particular organ. For example, the sinusoids in liver are formed, in part, by hepatocytes, which are unique to liver. Using the methods disclosed herein, in vivo panning can be used to identify molecules that selectively home to hepatocytes and specific homing can be demonstrated by performing the appropriate competition experiments.

An organ homing molecule such as a brain homing (Table 1) or kidney homing (Table 2) peptide can be used to direct a moiety to a selected organ by linking the moiety to the molecule. As used herein, the term "moiety" is used broadly to mean an agent linked to the organ homing molecule. A moiety can be, for example, a detectable label such a radiolabel; a toxin such as ricin; or a drug such as a chemotherapeutic agent. Various moieties and methods for linking a moiety to a molecule are well known in the art and commercially available (see, for example, Harlow and Lane, *Antibodies: A laboratory manual* (Cold Spring Harbor Laboratory Press 1988), which is incorporated herein by reference).

Linking of a moiety to an organ homing molecule for the purpose of directing homing of the moiety to the selected organ is exemplified by the linking of a brain homing peptide to a RBC, wherein the peptide directed homing of the RBC to brain (see Example II.D.). These results indicate that an organ homing molecule of the invention can be linked to other cell types in order to direct the cell type to a selected organ. For example, a tumor homing molecule identified by in vivo panning can be linked to a white blood cell (WBC) such as a cytotoxic T cell or a killer cell, wherein upon administration of the tumor homing molecule/WBC complex, the molecule directs homing of the WBC to the tumor, where the WBC can exert its effector function.

An organ homing molecule also can be linked to a moiety that is detectable external to the subject in order to perform an in vivo diagnostic imaging study. For example, in vivo imaging using a detectably labeled brain homing peptide can identify a region in the brain where circulation is occluded. For such studies, a gamma ray emitting radionuclide such as indium-111 or technitium-99 can be linked to a brain homing molecule and, following administration to a subject, can be detected using a solid scintillation detector. Alternatively, a positron emitting radionuclide such as carbon-11 or a paramagnetic spin label such as carbon-13 can be linked to the molecule and, following administration to a subject, the localization of the moiety/molecule can be detected using positron emission transaxial tomography or magnetic resonance imaging, respectively.

Such in vivo imaging methods also can be used to identify the presence of cancer in a subject by linking an appropriate moiety to a tumor homing molecule, which can recognize a unique target expressed by the tumor cells or by the blood vessels formed by angiogenesis in the tumor. Such methods can identify a primary tumor as well as a metastatic lesion, which may not be detectable using other methods. Having identified the presence of such cancer, the tumor homing molecule can be linked to a toxin or to a chemotherapeutic agent in order to direct the moiety to the tumor. Such a method can allow selective killing of the tumor, while substantially sparing normal tissues.

When administered to a subject, the molecule/moiety complex is administered as a pharmaceutical composition containing, for example, the complex and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the complex. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art would know that a pharmaceutical composition containing an organ homing molecule can be administered to a subject by various routes including, for example, orally or parenterally, such as intravenously The composition can be administered by injection or by intubation. The pharmaceutical composition also can be an organ homing molecule linked to liposomes or other polymer matrices, which can have incorporated therein, for example, a drug such as a chemotherapeutic agent (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

For the diagnostic or therapeutic methods disclosed herein, an effective amount of the molecule/moiety complex must be administered to the subject. As used herein, the term "effective amount" means the amount of the complex that produces the desired effect. An effective amount often will depend on the moiety linked to the organ homing molecule. Thus, a lesser amount of a radiolabeled molecule can be required for imaging as compared to the amount of a drug/molecule complex administered for therapeutic purposes. An effective amount of a particular molecule/moiety for a specific purpose can be determined using methods well known to those in the art.

The route of administration of an organ homing molecule will depend, in part, on the chemical structure of the molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). Such methods can be performed on peptides identified by in vivo panning. In addition, methods for preparing libraries of peptide analogs such as peptides containing D-amino acids; peptidomimetics consisting of organic molecules that mimic the structure of peptide; or peptoids such as vinylogous peptoids, are known in the art and can be used to identify molecules that home to a selected organ and are stable for oral administration.

Organ homing molecules obtained using the methods disclosed herein also can be useful for identifying a target molecule such as a cell surface receptor or a ligand for a receptor, which is recognized by the organ homing peptide. For example, an organ homing peptide can be linked to a solid support such as a chromatography matrix. The linked peptide then can be used for affinity chromatography by passing an appropriately processed sample of a selected organ over the column in order to bind a particular target molecule. The bound target molecule can be eluted from the column and can be identified and characterized by various well known methods. In addition, an organ homing peptide can be linked to a detectable moiety such as a radionuclide, a fluorescent molecule, an enzyme or biotin and can be used, for example, to screen a sample in order to detect the target molecule during various steps of purification of the target molecule.

The methods of the present invention were used to identify peptides that selectively home to a selected organ. For example, brain homing peptides such as CNSRLHLRC (SEQ ID NO: 1), CENWWGDVC (SEQ ID NO: 2), and others as shown in Table 1 were identified. In addition, brain homing peptides comprising the motif, SRL (serine-arginine-lysine), such as the peptide CLSSRLDAC (SEQ ID NO: 3), or the motif VLR, such as the peptide WRCVLREGPAGGCAWFNRHRL (SEQ ID NO: 16), were identified. Kidney homing peptides such as CLPVASC (SEQ ID NO: 21), CGAREMC (SEQ ID NO: 22) and other as shown in Table 2 also were identified.

Cysteine residues were included in the peptides such that cyclization of the peptides could be effected. However, in some cases one or both of the cysteine residues in a peptide can be deleted without significantly affecting the organ homing activity of a peptide of the invention. Thus, a peptide having the sequence LSSRLDA (SEQ ID NO: 19; compare SEQ ID NO: 3) also can be a brain homing peptide. Similarly, the amino acid residues N-terminal and C-terminal to the first and last cysteine residues, respectively, in a peptide such as WRCVLREGPAGGCAWFNRHRL (SEQ ID NO: 16) can be dispensable without substantially altering brain homing activity of the peptide. Thus, a peptide having the sequence VLREGPAGG (SEQ ID NO: 20) also can be useful as a brain homing peptide. Methods for determining the necessity of a cysteine residue or of amino acid residues N-terminal or C-terminal to a cysteine residue for organ homing activity of a peptide of the invention are routine and well known in the art.

An organ homing peptide is useful, for example, for targeting a desired moiety to the selected organ as discussed above. In addition, an organ homing peptide can be used to identify the presence of a target molecule in a sample. As used herein, the term "sample" is used in its broadest sense to mean a cell, tissue, organ or portion thereof that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which an organ homing molecule binds.

An organ homing peptide such as a brain homing peptide can be used to identify the target molecule expressed in brain. For example, a brain homing peptide can be attached to a matrix such as a chromatography matrix to produce a peptide affinity matrix. A homogenized sample of brain can be applied to the peptide-affinity matrix under conditions that allow specific binding of the brain homing peptide to the target molecule (see, for example, Deutshcer, Meth. Enzymol., Guide to Protein Purification (Academic Press, Inc., ed. M. P. Deutscher, 1990), Vol. 182, which is incorporated herein by reference; see, for example, pages 357–379). Unbound and non-specifically bound material can be removed and the specifically bound brain-derived target molecule can be isolated in substantially purified form.

The following examples are intended to illustrate but not limit the present invention.

EXAMPLE I

IN VIVO PANNING

This example demonstrates methods for preparing a phage library and screening the library using in vivo panning to identify phage expressing peptides that home to a selected organ.

A. Preparation of phage libraries:

Phage display libraries were constructed using the fuse 5 vector as described by Koivunen et al. (supra, 1995; see, also, Koivunen et al. *Meth. Enzymol.* 245:346–369 (1994b), which is incorporated herein by reference). Six libraries encoding peptides designated $CX_5C$ (SEQ ID NO: 36), $CX_6C$ (SEQ ID NO: 37), $CX_7C$ (SEQ ID NO: 38), $CX_9$ (SEQ ID NO: 39), $X_2CX_{14}CX_2$ (SEQ ID NO: 40) and $X_2CX_{18}$ (SEQ ID NO: 41) were prepared, where "C" indicates cysteine and "$X_N$" indicates the given number of individually selected amino acids These libraries can display cyclic peptides when at least two cysteine residues are present in the peptide.

Oligonucleotides were constructed such that "C" was encoded by the codon TGT and "$X_N$" was encoded by NNK, where "N" is equal molar mixtures of A, C, G and T, and where "K" is equal molar mixtures of G and T. Thus, the peptide represented by $CX_5C$ (SEQ ID NO: 36) can be represented by an oligonucleotide having the sequence TGT $(NNK)_5$TGT (SEQ ID NO: 42) Oligonucleotides were made double stranded by 3 cycles of PCR amplification, purified and ligated to the nucleic acid encoding the gene III protein in the fuse 5 vector such that, upon expression, the peptide is present as a fusion protein at the N-terminus of the gene III protein.

The vectors were transfected by electroporation into MC1061 cells. Bacteria were cultured for 24 hr in the presence of 20 µg/ml tetracycline, then phage were collected from the supernatant by precipitation twice using polyethylene glycol. Each library contained about $5\times10^9$ to $5\times10^{14}$ transducing units (TU; individual recombinant phage).

B. In vivo panning of phage:

A mixture of phage libraries containing $1\times10^{14}$ TU was diluted in 200 µl DMEM and injected into the tail vein of anesthetized BALB\c mice (2 month old females; Jackson Laboratories; Bar Harbor Me.); Avertin (0.015 ml/g) was used as anesthetic. After 1–4 minutes, mice were snap frozen in liquid nitrogen. To recover the phage, carcasses were partially thawed at room temperature for 1 hr, organs were collected and weighed, then were ground in 1 ml DMEM-PI (DMEM containing protease inhibitors (PI); phenylmethylsulfonyl fluoride (PMSF; 1 mM), aprotinin (20 µg/ml), leupeptin (1 µg/ml)).

Organ samples were washed 3 times with ice cold DMEM-PI containing 1% bovine serum albumin (BSA), then directly incubated with 1 ml K91-kan bacteria for 1 hr. Ten ml NZY medium containing 0.2 µg/ml tetracycline (NZY/tet) was added to the bacterial culture, the mixture was incubated in a 37° C. shaker for 1 hr, then 200 µl aliquots were plated in agar plates containing 40 µg/ml tetracycline (tet/agar).

Individual colonies containing phage recovered from brain or kidney were grown for 16 hr in 5 ml NZY/tet. The bacterial cultures obtained from the individual colonies were pooled and the amplified eluates were injected into mice as described above for a second round of in vivo panning. A third round of panning also was performed. Phage DNA was purified from individual bacterial colonies obtained from the second and the third round of in vivo panning and the DNA sequences encoding the peptides expressed by selected phage were determined (see Koivunen et al., supra, 1994b).

EXAMPLE II

CHARACTERIZATION OF PEPTIDES THAT HOME TO A SELECTED ORGAN

This example demonstrates that an organ homing peptide of the invention selectively homes to a selected organ and that an organ homing peptide identified by in vivo panning can be used to direct a moiety to a selected organ.

A. Brain is the selected organ

Three rounds of in vivo panning in mice were performed. Kidney was used as a control organ. Mice were injected with two different mixtures of phage libraries. The first mixture contained libraries encoding $CX_9$ (SEQ ID NO: 39), $CX_5C$ (SEQ ID NO: 36), $CX_6C$ (SEQ ID NO: 37) and $CX_7C$ (SEQ ID NO: 38) peptides ($CX_{5-7}/CX_9$ mixture; SEQ ID NOS: 36–39). The second mixture contained libraries encoding $X_2CX_{14}CX_2$ (SEQ ID NO: 40) and $X_2CX_{18}$ (SEQ ID NO: 41) peptides ($X_2CX_{18}/X_2CX_{14}CX_2$ mixture; SEQ ID NOS: 40 and 41)

The phage library mixtures were administered to mice via tail vein injection. Phage input was $1\times10^{16}$ TU of the $CX_{5-7}/CX_9$ (SEQ ID NOS: 36–39) mixture or $1\times10^{14}$ TU of the $X_2CX_{18}/X_2CX_{14}CX_2$ (SEQ ID NOS: 40 and 41) mixture. Phage were recovered from the brains of the injected mice, the recovered phage were amplified in vitro, then a second and a third round of in vivo panning was performed. During the second and third rounds of panning, phage were recovered from brain and from kidney and the number of TU from each organ was compared. This comparison revealed that 6× more phage from the $CX_{5-7}/CX_9$ (SEQ ID NOS: 36–39) mixture bound to brain than to kidney in the second round and 13× more of the $CXS_{5-7}/CX_9$ (SEQ ID NOS: 36–39) phage bound to brain than to kidney in the third round of panning. Following administration of the $X_2CX_{18}/X_2CX_{14}CX_2$ (SEQ ID NOS: 40 and 41) mixture, an 11× and 8× enrichment of phage homing to the brain as compared to kidney occurred during the second and third rounds of panning, respectively. Thus, substantial enrichment of phage binding to the brain was observed following the second and third rounds of in vivo panning.

The amino acid sequences were determined for the inserts present in 73 cloned phage that were recovered from brain during the second and third rounds of in vivo panning. Peptides containing an SRL motif predominated (36% of the clones sequenced; see SEQ ID NOS: 1, 3 and 5), followed by peptides containing the VLR motif (20.5% of the clones; see SEQ ID NOS: 4 and 16) and the peptide CENW-WGDVC (SEQ ID NO: 2; 19% of the clones; see Table 1).

Other peptides that occurred much less frequently, but were present more than once, included CGVRLGC (SEQ ID NO: 6), CKDWGRIC (SEQ ID NO: 7), CLDWGRIC (SEQ ID NO: 8) and CTRITESC (SEQ ID NO: 9). Nine other sequences appeared only one time each and were not characterized further.

TABLE 1

PEPTIDES FROM PHAGE RECOVERED FROM BRAIN

| A.A. SEQUENCE (SEQ ID NO:) | | # PHAGE DISPLAYING SAME A.A. SEQUENCE (% PHAGE) | |
|---|---|---|---|
| $CX_{5-7}C/CX_9$ (36–39) library: | | | |
| CNSRLHLRC | (1) | 16 | (21.9%) |
| CENWWGDVC | (2) | 14 | (19.2%) |
| CLSSRLDAC | (3) | 6 | (8.2%) |
| CVLRGGRC | (4) | 5 | (6.8%) |
| CNSRLQLRC | (5) | 4 | (5.5%) |
| CGVRLGC | (6) | 3 | (4.1%) |
| CKDWGRIC | (7) | 2 | (2.8%) |
| CLDWGRIC | (8) | 2 | (2.8%) |
| CTRITESC | (9) | 2 | (2.8%) |
| CETLPAC | (10) | 1 | (1.4%) |
| CRTGTLFC | (11) | 1 | (1.4%) |
| CGRSLDAC | (12) | 1 | (1.4%) |
| CRHWFDVVC | (13) | 1 | (1.4%) |
| CANAQSHC | (14) | 1 | (1.4%) |
| CGNPSYRC | (15) | 1 | (1.4%) |
| $X_2CX_{18}/X_2CX_{14}CX_2$ (SEQ ID NOS: 40 and 41) library: | | | |
| WRCVLREGPAGGCAWFNRHRL | (16) | 10 | (13.7%) |
| YPCGGEAVAGVSSVRTMCSE | (17) | 1 | (1.4%) |
| LNCDYQGTNPATSVSVPCTV | (18) | 1 | (1.4%) |

The SRL tripeptide motif was present in several different sequence contexts, indicating that the nucleic acids encoding the peptides were derived from a number of independent phage. These results indicate that the selection of the peptides containing the SRL motif represents the specific binding of several independent phage displaying peptides with the SRL sequence and is not an artifact due, for example, to phage amplification. In addition, in some cases, different phage expressed peptides that had the same amino acid sequence, but were encoded by oligonucleotides having different sequences, thus confirming that homing of a particular phage to an organ is due to the specific peptide expressed on the phage.

To determine the specificity of brain homing of the individual motifs identified, phage displaying the predominant motifs were amplified individually, diluted to the same input titer and administered to mice. Following administration, brain and kidney were removed and the number of TU of phage in each organ was determined. The enrichment ratio of phage recovered from the selected organ, brain, as compared to the control organ, kidney, revealed that phage displaying one of the four most recovered peptides, CNSRLHLRC (SEQ ID NO: 1), CENWWGDVC (SEQ ID NO: 2), WRCVLREGPAGGCAWFNRHRL (SEQ ID NO: 16), CLSSRLDAC (SEQ ID NO. 3), each selectively targeted the brain as compared to the kidney. Specifically, the ratio of selective homing (brain:kidney) was about 8 for CNSRLHLRC (SEQ ID NO: 1) and for CLSSRLDAC (SEQ ID NO: 3), 4 for CENWWGDVC (SEQ ID NO: 2) and 9 for WRCVLREGPAGGCAWFNRHRL (SEQ ID NO: 16). Two control phage showed low binding to both brain and kidney. These results demonstrate that in vivo panning can be used to screen phage display libraries in order to identify phage expressing peptides that home to a selected organ.

B. Kidney as the selected organ

The same methodology used to isolate phage expressing brain homing peptides was used to isolate phage expressing peptides that home to kidney. In these experiments, brain was used as the control organ. A mixture of the $CX_5C$ (SEQ ID NO: 36) and the $CX_6C$ (SEQ ID NO: 37) libraries was administered as described above. Homing of phage to the kidney was obtained and an approximately 3x to 7x enrichment of phage homing to kidney was observed following a second round of in vivo panning.

The amino acid sequences were determined for the inserts in 48 cloned phage that homed to kidney. The peptides expressed by these phage were represented by two predominant sequences, CLPVASC (SEQ ID NO: 21; 46% of the clones sequenced) and CGAREMC (SEQ ID NO: 22; 17% of the clones; see Table 2). In addition, the peptide CKGRSSAC (SEQ ID NO: 23) appeared three times and three other peptides were present twice each. Phage expressing a CLPVASC (SEQ ID NO: 21), CGAREMC (SEQ ID NO: 22) or CKGRSSAC (SEQ ID NO: 23) peptide each exhibited selective homing to kidney; the ratio of selective kidney:brain homing was 7 for CLPVASC (SEQ ID NO: 21), 3 for CGAREMC (SEQ ID NO: 22) and 2 for CKGRSSAC (SEQ ID NO: 23).

These results demonstrate that the in vivo panning method is a generally applicable method for screening a phage library to identify phage expressing peptides that home to a selected organ. Database searches did not reveal any significant homology of the

TABLE 2

PEPTIDES FROM PHAGE RECOVERED FROM KIDNEY

| A.A. SEQUENCE (SEQ ID NO:) | | # PHAGE DISPLAYING SAME A.A. SEQUENCE (% PHAGE) | |
|---|---|---|---|
| CLPVASC | (21) | 22 | (45.8%) |
| CGAREMC | (22) | 8 | (16.7%) |
| CKGRSSAC | (23) | 3 | (6.2%) |
| CWARAQGC | (24) | 2 | (4.2%) |
| CLGRSSVC | (25) | 2 | (4.2%) |
| CTSPGGSC | (26) | 2 | (4.2%) |
| CMGRWRLC | (27) | 1 | (2.1%) |
| CVGECGGC | (28) | 1 | (2.1%) |
| CVAWLNC | (29) | 1 | (2.1%) |
| CRRFQDC | (30) | 1 | (2.1%) |
| CLMGVHC | (31) | 1 | (2.1%) |
| CKLLSGVC | (32) | 1 | (2.1%) |
| CFVGHDLC | (33) | 1 | (2.1%) |
| CRCLNVC | (34) | 1 | (2.1%) |
| CKLMGEC | (35) | 1 | (2.1%) | brain homing or kidney homing peptides to known ligands for endothelial cell receptors.

C. Peptide homing is specific:

In order to confirm the specificity of a peptide for directing homing to a selected organ, peptide competition experiments were performed. The cyclic peptide, CLSSRLDAC (SEQ ID NO: 3), which is one of the brain homing peptides (see Table 1) was synthesized (Immunodynamics; La Jolla Calif.) and purified by HPLC. The effect on the homing of phage expressing CLSSRLDAC (SEQ ID NO: 3), CENWWGDVC (SEQ ID NO: 2) or WRCVLREGPAGGCAWFNRHRL (SEQ ID NO: 16) to the brain was examined in order to determine whether co-administration of the synthetic peptide affected homing of the phage.

Phage expressing CLSSRLDAC (SEQ ID NO: 3), CENWWGDVC (SEQ ID NO: 2) or WRCVLREGPAGGCAWFNRHRL (SEQ ID NO: 16) were titrated to the same concentration and 1×10⁸ TU was injected into mice alone, or with 100 μg purified synthetic cyclic CLSSRLDAC (SEQ ID NO: 3) peptide. The synthetic CLSSRLDAC (SEQ ID NO: 3) peptide inhibited the homing of phage expressing CLSSRLDAC (SEQ ID NO: 3) by about 60%. This result demonstrates that the homing of the phage to brain is specifically due to the expression on the phage of the CLSSRLDAC (SEQ ID NO: 3) peptide.

The synthetic CLSSRLDAC (SEQ ID NO: 3) peptide also inhibited homing of phage expressing the WRCVLREG-PAGGCAWFNRHRL (SEQ ID NO: 16) peptide by about 60%, but did not affect homing of CENWWGDVC (SEQ ID NO: 2) phage. This result indicates that the CLSSRLDAC (SEQ ID NO: 3) and WRCVLREGPAGGCAWFNRHRL (SEQ ID NO: 16) peptides can recognize the same target molecule in brain, whereas the CENWWGDVC (SEQ ID NO: 2) peptide recognizes a different target.

D. The brain homing peptide CLSSRLDAC (SEQ ID NO: 3) directs red blood cells to brain The synthetic cyclic CLSSRLDAC (SEQ ID NO: 3) peptide (1 mg) was labeled with iodine-125 using the Bolton and Hunter reagent (Amersham; Arlington Heights Ill.). Labeled peptide was purified by reverse phase HPLC on Sep-Pak™ cartridges (Waters, Millipore Corp.; Milford Pa.) and the $^{125}$I-peptide (200 μg) was coupled to 1 ml glutaraldehyde-stabilized sheep RBC (Sigma Chemical Co.; St. Louis Mo.) according to the manufacturer's instructions.

Fifty μl $^{125}$I-peptide/RBC (200,000 cpm), alone or with 10 mM of unlabeled CLSSRLDAC (SEQ ID NO: 3), which is a brain homing peptide, or CVRLNSLAC (SEQ ID NO: 43), which has no brain homing activity, was injected into the tail vein. After 2 min, each mouse was perfused through the heart with 50 ml DMEM and the brain and kidney were removed and assayed for radioactivity.

Approximately twice as much of the CLSSRLDAC/RBC complex (SEQ ID NO: 3) homed to brain than to kidney. Coadministration of unlabeled CLSSRLDAC (SEQ ID NO: 3) with the complex essentially completely inhibited brain homing of the complex but had no effect on complex localizing to the kidney, indicating that localization of the complex in the kidney was non-specific. Coadministration of unlabeled CVRLNSLAC (SEQ ID NO: 43) had no effect on selective homing of the complex to brain and no effect on the non-specific localization of the complex in the kidney. These results demonstrate that an organ homing peptide identified using in vivo panning can be linked to a moiety such as a blood cell and selectively directs homing of the linked moiety to the selected organ.

Although the invention has been described with reference to the disclosed examples, it should be understood that various modifications can be made without departing from the spirit of the invention. Accordingly, the invention is limited only by the following claims.

We claim:

1. An enriched library fraction containing a plurality of molecules that selectively home to a selected organ or tissue, said enriched library fraction recovered by in vivo panning, comprising the steps of:
   a) administering to a subject a library of diverse molecules, wherein each of said molecules is attached to a tag that facilitates recovery of said molecules;
   b) collecting a sample of the selected organ or tissue; and
   c) recovering from said sample said enriched library fraction containing a plurality of molecules that selectively home to said selected organ or tissue,
wherein said library of diverse molecules is not a nucleic acid library.

2. The enriched library fraction of claim 1, wherein said selected organ or tissue is brain.

3. The enriched library fraction of claim 1, wherein said selected organ or tissue is kidney.

4. The enriched library fraction of claim 1, wherein said organ or tissue is a tumor.

5. The enriched library fraction of claim 1, wherein said molecules are s elected from the group consisting of peptides, peptidomimetics, proteins and fragments of proteins.

6. An enriched library fraction containing a plurality of molecules that target the vasculature of a selected organ or tissue, said enriched library fraction recovered by in vivo panning, comprising the steps of:
   a) administering to a subject a library of diverse molecules, wherein each of said molecules is attached to a tag that facilitates recovery of said molecules;
   b) collecting a sample of the selected organ or tissue; and
   c) recovering from said sample said enriched library fraction containing a plurality of molecules that target the vasculature of said selected organ or tissue,
wherein said library of diverse molecules is not a nucleic acid library.

7. The enriched library fraction of claim 6, wherein said selected organ or tissue is brain.

8. The enriched library fraction of claim 6, wherein said selected organ or tissue is kidney.

9. The enriched library fraction of claim 6, wherein said organ or tissue is a tumor.

10. The enriched library fraction of claim 6, wherein said molecules are selected from the group consisting of peptides, peptidomimetics, proteins and fragments of proteins.

* * * * *

UNITED STATES PATENT AND TRADEMARK OFFICE
CERTIFICATE OF CORRECTION

PATENT NO. : 6,296,832 B1
DATED : October 2, 2001
INVENTOR(S) : Ruoslahti et al.

It is certified that error appears in the above-identified patent and that said Letters Patent is hereby corrected as shown below:

<u>Title page,</u>
Item [63], please delete "Jun. 23, 1997," and replace with -- May 23, 1997, --.

<u>Column 1,</u>
Line 5, please delete "Jun. 23, 1997," and replace with -- May 23, 1997, --.
Line 50, please delete "antibody Upon" and replace with -- antibody. Upon --.

<u>Column 7</u>
Line 46, please delete "phox" and replace with -- phOx --.

<u>Column 37, claim 5,</u>
Line 31, please delete "s elected" and replace with -- selected --.

Signed and Sealed this

Nineteenth Day of March, 2002

Attest:

*Attesting Officer*

JAMES E. ROGAN
*Director of the United States Patent and Trademark Office*